United States Patent [19]

Weissman

[11] Patent Number: 5,183,397
[45] Date of Patent: Feb. 2, 1993

[54] DENTAL BONDING ARRANGEMENT AND METHOD

[76] Inventor: Bernard Weissman, 225 E. 48th St., New York, N.Y. 10017

[21] Appl. No.: 409,726

[22] Filed: Sep. 20, 1989

[51] Int. Cl.[5] ............................................. A61C 5/08
[52] U.S. Cl. ................................... 433/215; 433/218; 433/223; 433/226
[58] Field of Search ............... 433/226, 223, 215, 218, 433/180, 9

[56] References Cited

U.S. PATENT DOCUMENTS

| | | | |
|---|---|---|---|
| 1,265,581 | 5/1918 | Zurbrigg | 433/39 |
| 2,659,970 | 11/1953 | Ingersoll, Jr. | 433/213 |
| 3,250,003 | 5/1966 | Collito | 433/9 |
| 3,265,202 | 8/1966 | Cornell | 433/202.1 |
| 4,204,325 | 5/1980 | Kaelble | 433/9 |
| 4,674,980 | 6/1987 | Ibsen et al. | 433/228.1 |
| 4,909,736 | 3/1990 | Ritter | 433/226 |
| 4,919,615 | 4/1990 | Croll | 433/3 |
| 4,952,142 | 8/1990 | Nicholson | 433/9 |
| 5,015,180 | 5/1991 | Randklev | 433/215 |

*Primary Examiner*—John J. Wilson
*Attorney, Agent, or Firm*—Helfgott & Karas

[57] ABSTRACT

A dental bonding arrangement for use in attaching a dental prosthesis onto a dental surface. The bonding arrangement includes a self-supporting, semi-rigid layer of adhesive material positioned between a pair of opposing backing sheets. The adhesive material is of sufficient viscosity to permit contouring of the adhesive along the dental surface, and yet of sufficient rigidity to maintain itself erect on the dental surface without flowing. The backing sheets are selectively removed to initially place the adhesive film on the dental surface and, after being positioned, removing the opposing backing sheet and then placing of the dental prosthesis. The particular dental prosthesis can be a porcelain inlay, a dental bracket, or the like.

14 Claims, 8 Drawing Sheets

DENTAL BONDING ARRANGEMENT AND METHOD

BACKGROUND OF THE INVENTION

This invention relates to dental bonding and more particularly to a dental adhesive material in the form of a sheet of semi-rigid, self-sustaining adhesive material sandwiched between two layers of backing material for use in bonding a dental inlay or a crown to a dental surface.

Dental bonding materials are prevalently utilized throughout the field of dentistry for securing crowns and restorative material onto dental surfaces. Numerous types of bonding materials are readily available including various composites, glass ionomers, and other chemicals which have been suggested. All of these are generally in the form of a paste or liquid which is typically applied onto the prosthesis and then the prosthesis pressed onto the dental surface. In utilizing such bonding materials, because of the fluid nature of the adhesive, it is not possible to obtain a uniform thickness of application between the inlay or a crown and the dental surface. This can cause an uneveness and frequently may shift the theoretical placement of the inlay from its actual desired locations on the dental surface.

Additionally, since the adhesive is generally in a liquid or paste state, there may be voids in the application of the adhesive on the inlay and the voids remain between the inlay and the dental surface. This may cause decay in the voids as well as disturbing the retention of the dental inlay.

Additionally, with the use of the adhesive liquid or paste bonding material, the material may squeeze out beyond the dental inlay and it is a difficult procedure to remove the adhesive and achieve a proper seal at the boundary between the inlay and the dental surface. This is even further complicated when the marginal edge occurs at the gum interface where adequate trimming and shaping of edges becomes difficult.

The problem of utilizing a paste or liquid is even further compounded in connection with aesthetic dentistry in which veniers are applied onto cut-down dental enamel. In this procedure, the existing enamel is initially reduced by minimal thicknesses, and typically, a porcelain inlay is then produced to seat into the reduced area of the enamel. Very thin layers of adhesive are needed to apply the inlay. With the use of existing adhesive pastes or liquids, voids are generally found in the interface. Likewise, when utilizing liquid or paste bonding material, the paste is applied onto the porcelain inlay and then the inlay pressed onto the dental surface. There is a shifting that may occur between the inlay and the dental surface in trying to position the inlay properly. Additionally, because of the uneven placement of the adhesive, as the adhesive squeezes out beyond the inlay there may be an uneven accumulation on one side of the tooth more than the other side causing inter-tooth spacing to be uneven.

This problem is even more compounded in the use of a porcelain inlay for posterior teeth. In order to permit adequate fit, the inlay is usually oversized to accommodate the adhesive material. As the application of the inlay occurs, shifting of the inlay causes uneven interspacing between adjacent teeth.

In addition to the problems resulting from utilization of the liquid or paste bonding materials, frequently there is also a problem of adequate retention with such material. While bonding materials being developed continue to provide improved retention capabilities, these are limited to chemical bonding capabilities. Little, if any, attention has been given to mechanical bonding in conjunction with the chemical bonding.

Further problems with existing bonding chemical agents concern the accurate placement of the dental prosthetic. By way of example, in the case of placement of a porcelain inlay, while the enamel of the dental surface may have been cut down, there may still be movement while placing of the inlay and accurate positioning is often difficult. Suitable physical mating structure would be helpful to provide accurate placement of the inlay without interfering with the proper adhesion and securement of the inlay.

Additional problems occur in connection with the placement of a peripheral crown about a cut-down tooth. Typically, a profile is formed about the tooth on which the crown will fit. Existing arrangements often cause difficulty in proper seating of the crown, especially at the lower edge meeting the gum line where a feathering effect occurs at the rather sharp edge of the crown which can bite into the gum line. Especially with existing bonding agents, there is a tendency to slide or shifting of the crown on the tooth surface which can cause cutting into the gum. Likewise, existing bonding agents fail to provide any mechanical bonding but rely exclusively on the chemical bonding effect of the material.

Accordingly, while there continues to be development in the field of bonding agents, further improvement in the bonding arrangements of a dental inlay onto a dental surface appears to be appropriate.

SUMMARY OF THE INVENTION

Accordingly, it is an object of the present invention to provide improved bonding techniques for use in securing a dental inlay or a crown onto a dental surface.

Yet, another object of the present invention is to provide improvements in bonding inlays onto dental surfaces.

Yet, another object of the present invention is to provide appropriate bonding techniques which utilize both chemical and mechanical bonding arrangements for securing a dental inlay onto a dental surface.

A further object of the present invention is to provide an improved bonding technique which also serves to accurately position the dental inlay onto the dental surface while improving the bonding relationship therebetween.

Still a further object of the present invention is to provide an improved bonding arrangement which permits a uniform thickness of adhesive to be applied between the dental inlay and the dental surface to thereby improve the bonding between the surfaces.

A further object of the present invention is to provide an improved bonding arrangement whereby the adhesive material utilized forms a gasket peripherally around the marginal edge of the dental inlay or crown as it is secured onto the dental surface.

Still another object of the present invention is to provide an approved bonding arrangement which reduces the shifting possibility between the dental inlay and the dental surface on which it is being bonded.

Another object of the present invention is to provide an approved bonding arrangement which permits appropriate trimming peripherally around the dental inlay which is being secured onto a dental surface.

A further object of the present invention is to provide an improved arrangement for seating a crown onto a profiled tooth which provides a secure seating for the crown and improves the retention of the crown on the tooth while providing for appropriate feeling between the crown and the tooth.

Briefly, in accordance with the present invention, there is provided a dental bonding arrangement for attaching a dental inlay onto a dental surface. The bonding arrangement includes a semi-rigid, self-sustaining film of adhesive material having at least one backing sheet thereon for supporting the film of adhesive material in a stored condition and from which the backing material can be removed upon application of the adhesive film onto dental surface. The adhesive material has sufficient viscosity to permit contouring of the adhesive material onto the dental surface. At the same time, it has sufficient rigidity to retain itself in a nonflowing state upon its application onto the dental surface.

In an embodiment of the invention, a second backing sheet is provided on the adhesive film to sandwich the film between the layers of the backing sheets and thereby permit its storage. The first backing sheet is removed and the adhesive film applied onto the dental surface, and after suitably positioning it and contouring it to the shape desired, the second backing sheet is removed whereupon the dental inlay can be pressed onto the adhesive.

In an embodiment of the invention, the adhesive material is of the light curing type whereupon application of light will cause the adhesive material to suitably bond the dental inlay onto the dental surface.

Where is an inlay is being applied onto the dental surface, the dental surface can also be prepared with at least one torroidal indent which aids in the positioning and retention of the inlay onto the dental surface. In such cases, the adhesive film can be of sufficient viscosity to be pressed into the indents. In another embodiment, the inlay can be formed with torroidal plugs which fit into the torroidal indents and the adhesive layer squeezes into the indents by means of the torroidal plugs on the inlay.

Yet, in further embodiment of the invention, the adhesive film itself can be in the form of a torroidal plug which can be sandwiched between layers of backing sheets. Individual ones of these adhesive plugs can be inserted into the torroidal indents and then another adhesive film layer applied uniformly thereon. Alternately, the film layer can be constructed with projecting torroidal plugs which can then be fit into the torroidal indents.

In yet a further embodiment, the adhesive film can be in the form of a circular ring or an elongated strip which can be wound around into a circular ring. In such situations, the adhesive film is used as a gasket to aid in the seating and retention of a crown on a profiled tooth. To aid in the seating of the crown, a flat ledge can be formed at the lower edge of the tooth near the gingiva. The ledge can include an undercut. A corresponding mating groove can be cast or formed into the crown thereby providing a pair of facing channels to define a recess in which the adhesive film can be inserted. In this manner, the ledge forms a lower seat for the crown. The adhesive film serves not only to retain the crown in bonded at engagement with the tooth, but also serves as an interlock between the crown and the tooth. Since the film can be squeezed as the crown is applied, it will flow along the bottom ledge and thereby also provide a gasket for sealing the crown onto the tooth.

Other types of dental attachments can also be coupled to a dental surface with such bonding arrangements such as dental brackets for use in orthodontic wire systems.

The aforementioned objects, features and advantages of the invention will be more fully described by the following detailed description of the invention taken in conjunction with the drawings which form and enter a part thereof.

BRIEF DESCRIPTION OF THE DRAWINGS

In the drawings.

In the various figures of the drawing, like reference characters designate like parts.

DESCRIPTION OF THE PREFERRED EMBODIMENT

Figure 1:
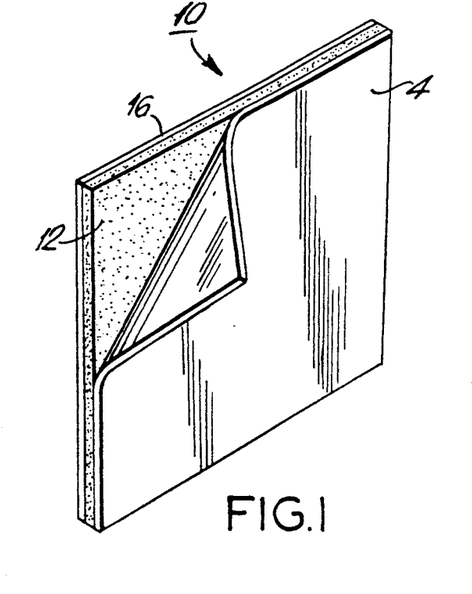
FIG. 1 is a perspective view showing the dental bonding arrangement of the present invention including a layer of adhesive material sandwiched between removable backing sheets.

Referring now to FIG. 1, there is generally shown the bonding arrangement of the present invention at 10 which includes a thin film or sheet of adhesive material 12 sandwiched between opposing backing sheets 14, 16. The backing sheets are typically of mylar, or other well-known material which can be peeled off thereby exposing the opposing surfaces of the adhesive film or sheet material. The adhesive material can be any of the well-known bonding materials presently available including, but not limited to, composites, resins, glass ionomers, etc. The adhesive material is formed of a suitable consistency and even thickness. It is of sufficient viscosity to permit it to be shaped and managed so as to conform it to the dental surface on which it is applied. At the same time, it is of sufficient self-supporting rigidity to prevent its flowing along the tooth surface. It will remain fixed and secured onto the surface, but yet permits manageability to shape it and to properly define it.

The particular type of adhesive can be either of the light curing type or of any other curing arrangement. If it be of the light curing type, typically, upon application of light through a fiber optic or other light transporting medium, it will readily bond as it cures. However, it should be appreciated that it can, likewise, be of other types such as a self-curing type in which case it can be dipped into various acceleration chemicals before being used.

The material can be cut and easily configured to conform to the periphery of any desired shape. Additionally, while it is shown in FIG. 1 in a substantially square configuration, it should be appreciated that it can be provided in any other shape or configuration, as will hereinafter be described.

Typically, the thickness will be between 5-20 microns. However, the thickness is limited more by the availability of area between the prosthesis and the dental surface. In the case of applying inlays, minimal thicknesses would be provided. On the other hand, in the case of bracket placement, typically, a thicker adhesive film would be needed, especially for lingual placement of the brackets.

Figure 2:
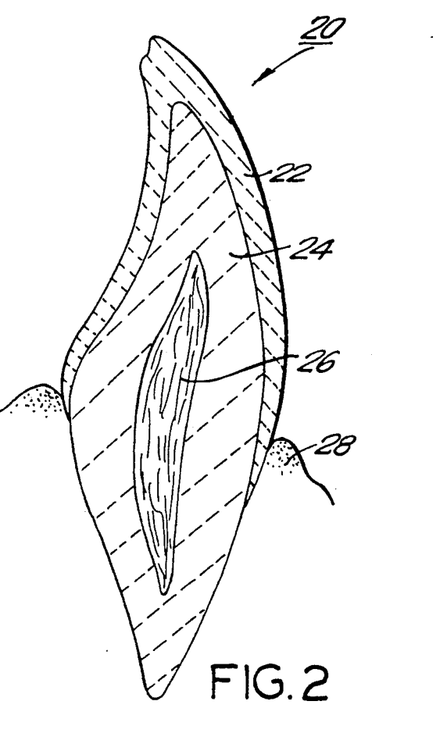
FIGS. 2-8 show various steps in applying an inlay onto a dental surface, using the bonding arrangement of FIG. 1.

Referring now to FIGS. 2-8, there will be described a method utilizing the present bonding arrangement in connection with the application of an inlay onto a dental surface. Referring now to FIG. 2, there is shown in cross-section a dental structure 20 having an external layer of enamel 22 covering the internal dentin 24. The central pulp area 26 is generally shown in the mid portion of the dentin. The dental structure 20 is embedded within the gum structure 28.

Figure 3:
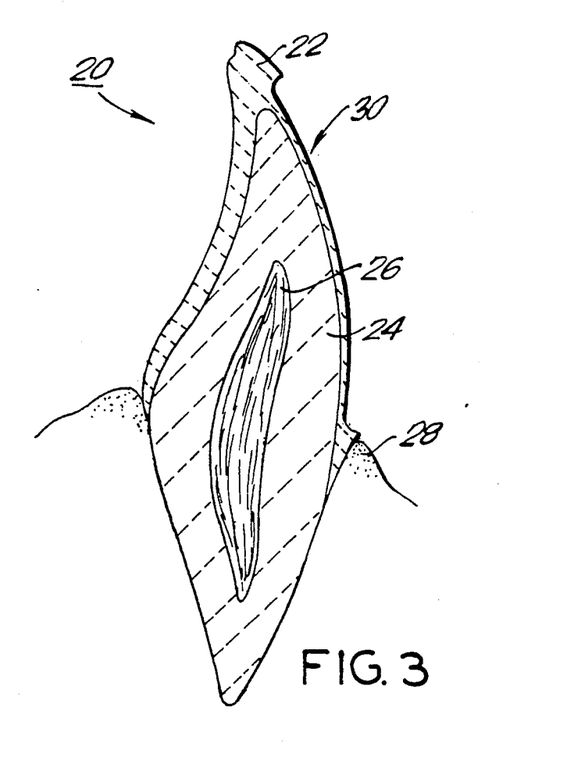

As the first step in applying porcelain inlay, a surface 30 is recessed within the enamel 22, as shown in FIG. 3. The recess is generally spaced from the lower gum area 28 to permit a lower edge line above the gum surface.

Figure 4:
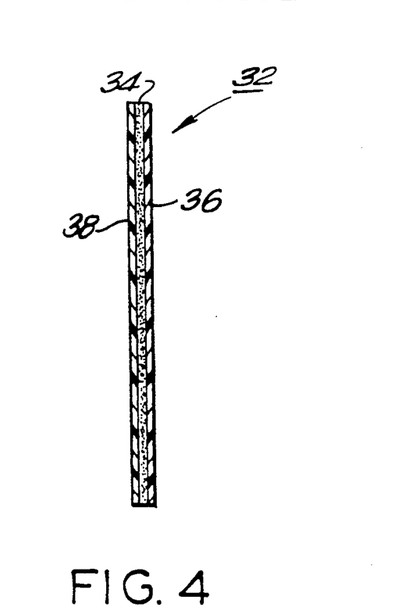

A bonding arrangement 32, shown in FIG. 4, includes a central adhesive film 34 sandwiched between opposing backing sheets 36, 38. The particular shape of the bonding arrangement can be such as to correspond to the shape of the recess and may be approximately 9 mm×4 mm. It should be appreciated, however, that the particular size and shape can be varied as desired.

Figure 5:
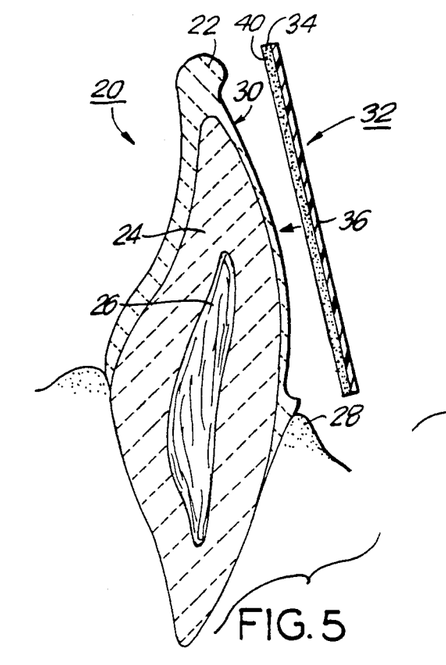

In utilizing the bonding arrangement of FIG. 4, initially one of the backing sheets, typically layer 38, will be peeled off to expose one surface 40 of the adhesive film 34, as shown in FIG. 5. The exposed surface 40 of the adhesive film 34, is then pressed against the recessed portion 30 of the enamel 22 of the tooth structure 20, as shown in FIG. 5.

With the backing sheet 36 remaining in place, the adhesive material 34 is sufficiently pliable to permit it to be pushed into and shaped onto the recessed surface 30. As can be seen at the upper and lower edges 42, 44, the adhesive film can be appropriately shaped to conform to the marginal edges of the recess 30.

At the same time, it will be appreciated that the adhesive film 34 is such as to provide a substantially uniform thickness along the entire recess.

Figure 6:
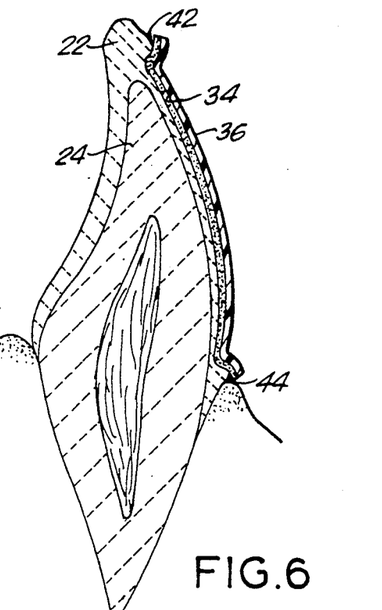
Figure 7:
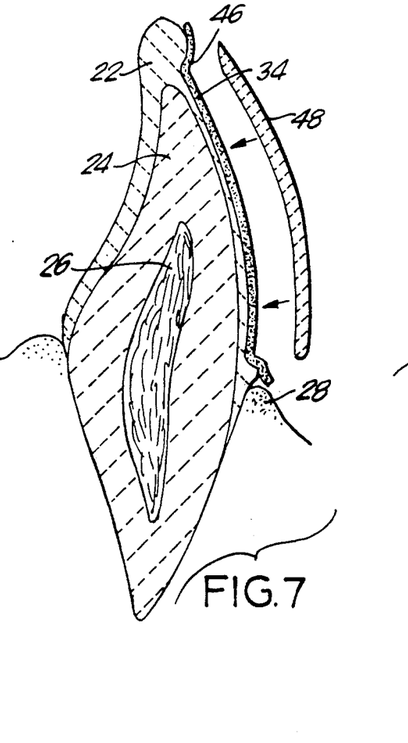

Once the adhesive film has been appropriately positioned, the outer backing sheet 36 can be peeled off to expose the outer adhesive surface 46 of the adhesive film 34. A suitably prepared porcelain inlay 48 which substantially conforms to the recess formed on the dental surface is then positioned over the adhesive surface 46 and pressed onto the adhesive film, as shown in FIG. 7.

Figure 8:
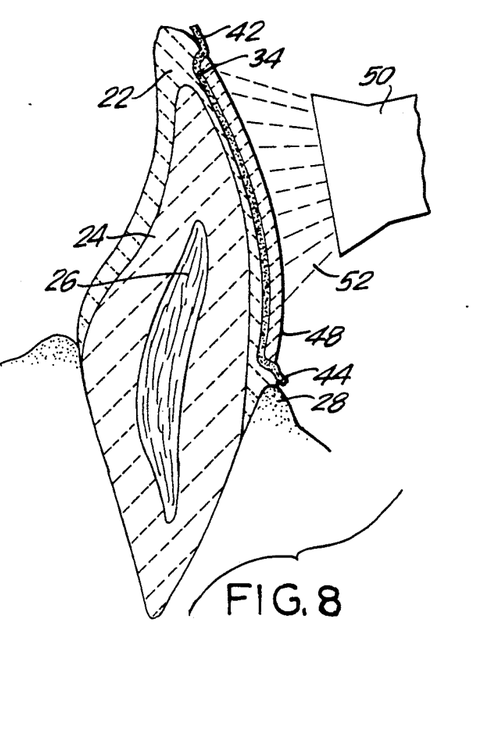

In the particular example shown, the adhesive film 34 is of a light curing type. As shown in FIG. 8, a fiber optic 50 is utilized to apply a sufficient amount of light 52 which passes through the enamel inlay 48 and light cures the adhesive material 34 thereby providing a suitable bonding between the inlay and the adhesive film.

It will be noted, that the adhesive film is of sufficient viscosity to permit it to be placed onto the dental surface and be shaped. At the same time, it is sufficiently rigid so that it remains in place and does not flow by itself. Furthermore, even upon application of the inlay and pressing of the inlay onto the film, it will not serve to squeeze out the adhesive and destroy its uniformity but, on the other hand, it will remain substantially uniform and consistent throughout the interface between the inlay and the dental surface. The adhesive film extends beyond the edges, as shown at 42, 44 to provide an inherent gasket around the marginal edge of the inlay thereby adequately sealing the inlay in place.

Figure 9:
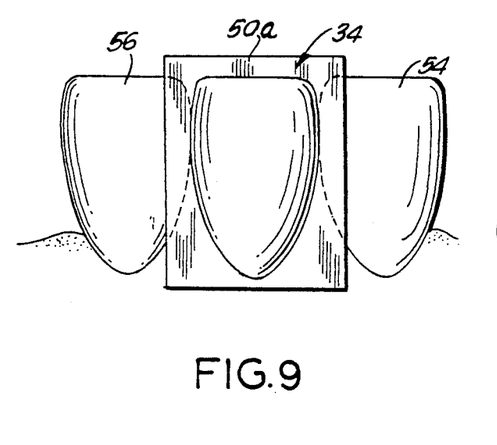
FIGS. 9 and 10 show the trimming of the adhesive material positioned under an inlay in order to provide desired spacing between adjacent teeth.

As shown in FIG. 9, the initial film 34 was of substantially rectangular shape. Upon application of the porcelain inlay 48, the periphery of the film 50a extends beyond the edges of the porcelain inlay. This edging can then be trimmed as desired. Typically, such trimming would take place even before curing. In fact, the trimming can take place in a possible two-step arrangement with the initial trim taking place before the curing and the ultimate trimming taking place after final positioning and curing.

Figure 10:
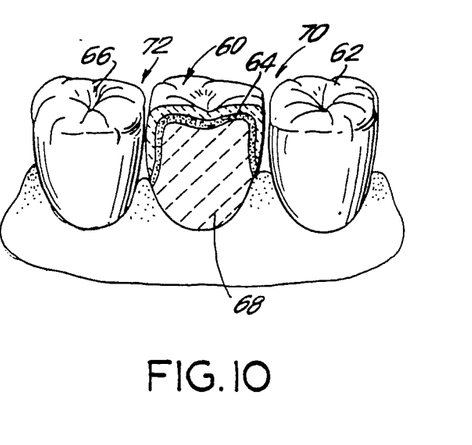

Referring to FIG. 10, wherein an additional benefit of the use of the present bonding arrangement can be appreciated. When dealing with posterior teeth, the porcelain inlay is typically made as a overcovering, as shown at 60 in FIG. 10. In such situations, because the adhesive layer 64 is of uniform thickness, there will be no shifting between the inlay 60 in positioning it on the tooth 68. As a result, the inter-tooth spacing 70 between the tooth 68 and the adjacent tooth 62 remains adequate as does the spacing 72 between the tooth 68 and the other adjacent tooth 66. In prior situations, because the material was such that it could be squeezed being generally of a liquid or paste the application of the material would be non-uniform and there would be shifting in trying to place the inlay 60. This would cause uneven spacing and frequently cause inadequate inter-tooth spacing.

Figure 11:
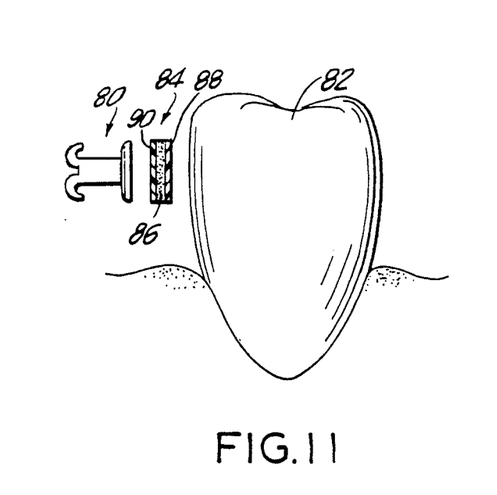
FIGS. 11 and 12 show the use of the bonding arrangement in the placement of an orthodontic bracket onto a dental surface.
Figure 12:
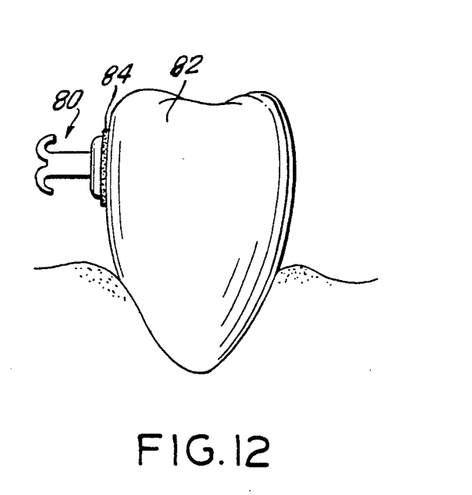

The present dental bonding arrangement can be utilized for other types of dental attachments as well. As shown in FIGS. 11 and 12, a dental bracket 80 for use in placement of an orthodontic system can also be bonded onto a tooth surface 82 by means of the bonding arrangement 84. Here again, there would be utilized an adhesive film 86 sandwiched between backing sheets 88, 90. Initially, the sheet 88 would be removed and the adhesive film 86 positioned onto the tooth surface. After proper positioning, the outer backing sheet 90 would then be removed and a bracket 80 would be secured onto the adhesive film 84. If of the light curing type, the material would then be exposed to light and the bond secured.

It should be appreciated that while light bonding material has been described, other types of materials can be utilized. For example, the adhesive can be of the self-curing type and the material left to stand until it adequately cures. Because the material will not flow, the weight of the inlay will be such that it will not cause shifting or movement even though it remains in place while it is being cured. Of course, additional chemicals can be utilized in order to accelerate the curing process.

In the case of light curing material, it should be appreciated that because of the presence of the backing sheets, even if the adhesive film is exposed to light such as daylight, it will generally not cure. The light curing time in daylight is quite lengthy and with the presence of the backing sheet, this time is even further extended to prevent curing. However, once the backing sheets are removed, and once a suitable fiber optic is utilized to expose the adhesive film, the curing process will be expedited.

Figure 13:
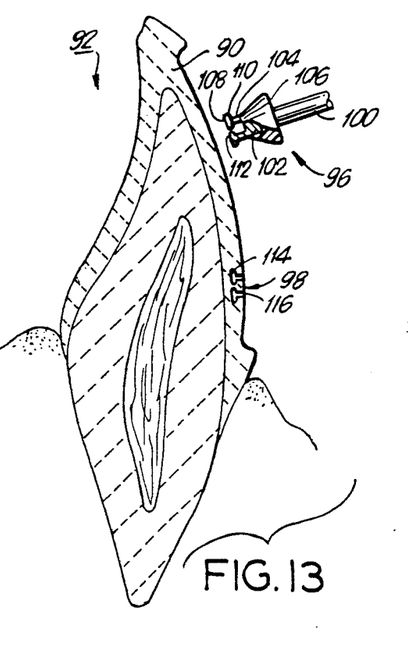
FIG. 13 shows the formation of a torroidal indent on the cut-down tooth surface to provide accurate placement and improved retention.
Figure 14:
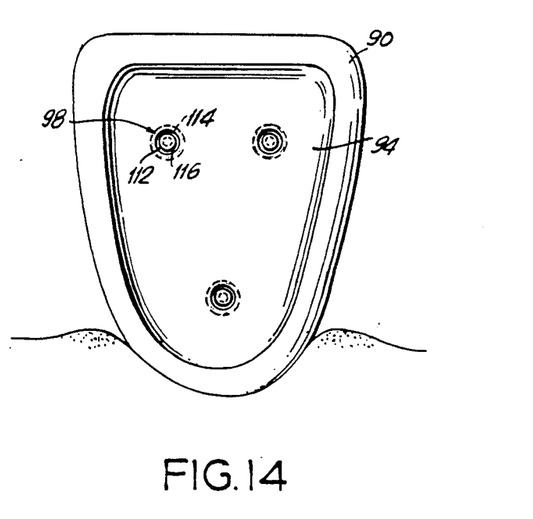
FIG. 14 shows a facial view of the resulting indents formed on the recessed surface.

In order to further enhance both the retention capability as well as to provide accurate placement of the inlay, in addition to cutting a recess in the enamel, placement indents are provided. As shown in FIGS. 13 and 14, after the enamel 90 on the tooth 92 has been cut down to form the recess 94, an appropriate tool 96 is utilized to form one or more donought or torroidal shaped indents 98. The tool typically includes a shank portion 100 with a forward cutting tool 102 having a torroidal shaped lower portion 104. A plastic sheath 106 limits the depth of cutting into the enamel. The bottom surface 108 contains an abrasive material which slightly projects laterally on the outer and inner edges 110, 112.

The tool is inserted into the enamel to cut a small indent, in the order of 0.05 mm, or the like. As the tool is inserted, when it reaches the lower limit which is designed by the lower shoulder edge of the plastic sheath 106, the tool is slightly moved laterally in order to provide the undercuts.

As is shown in FIGS. 13 and 14, the particular indent 98 includes a torroidal shaped groove 112 with the undercuts 114 at the outer edge and 116 at the inner edge. Typically, three such indents 98 can be provided on a dental surface. The indents are located in triangular configuration to provide proper securement of the inlay into the recess 94.

Figure 15:
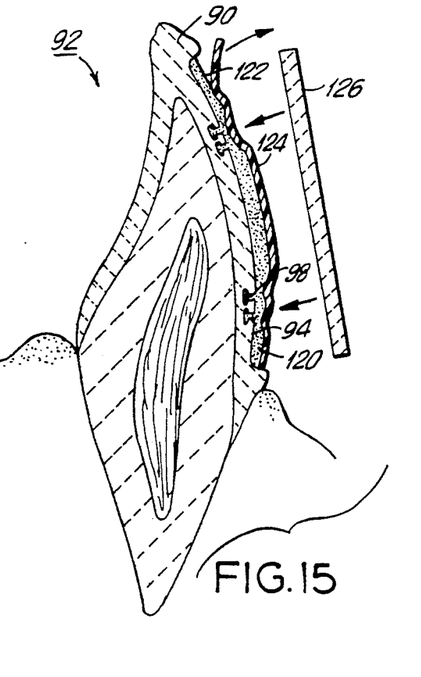
FIG. 15 shows the use of the bonding arrangement in conjunction with the torroidal indents to secure an inlay.

When utilizing the torroidal indents, the present bonding arrangement can find unique applicability. Specifically, and with reference now to FIG. 15, there is shown that the adhesive material 120 with its backing sheet 122 which has been positioned over the recess 94 containing the torroidal indents 98. The adhesive material can be squeezed and pushed in place to not only fill the recess 94 in the enamel 90, but also to fill the indents 98. The first backing sheet, of course, was removed prior to application of the adhesive film onto the tooth surface. The outer backing sheet 124 is then removed and the inlay 126 applied in place.

Figure 16:
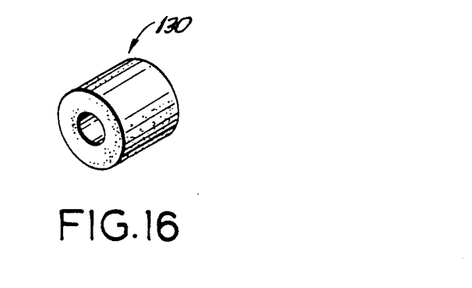
FIG. 16 shows an adhesive plug for use in conjunction with the torroidal indents.
Figure 17:
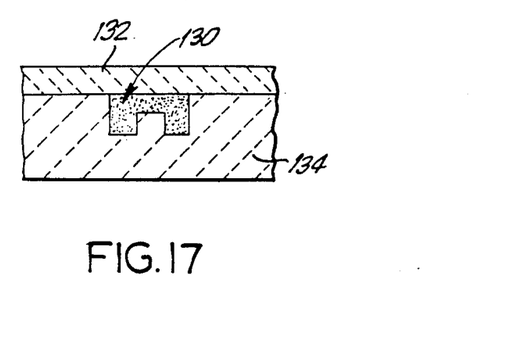
FIG. 17 shows the storage of the adhesive plug as a thin layer sandwiched between backing sheets, in accordance with the present invention.

Alternately, with reference now to FIGS. 16 and 17, there can be formed adhesive plugs 130 having a torroidal shape. The plug itself can be formed as a film with an outer backing sheet 132 and an inner backing sheet 134. Because of the unique shape, the backing sheet 134 can be made thicker and have the torroidal adhesive material embedded therein. Each of the backing sheets again can be individually removed and the torroidal adhesive plug 130 positioned in the torroidal indent.

Figure 18:
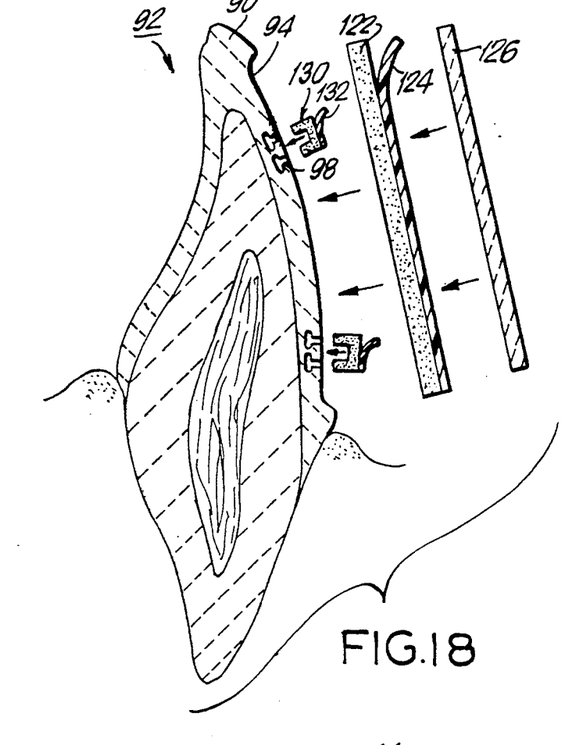
FIG. 18 shows the use of the plugs of FIG. 17 in conjunction with the bonding arrangement of FIG. 1 for the positioning of an inlay onto a dental surface.

As shown in FIG. 18, the torroidal plugs 130 initially fill the torroidal indents 98 formed on the recessed enamel surface 94. After the torroidal plugs are in place, the backing sheets 132 will be removed and the regular adhesive layer 122 applied. Its first backing sheet would first be removed and, after it is secured in place, the second backing sheet 124 is removed whereupon the inlay 126 is positioned in place.

Figure 19:
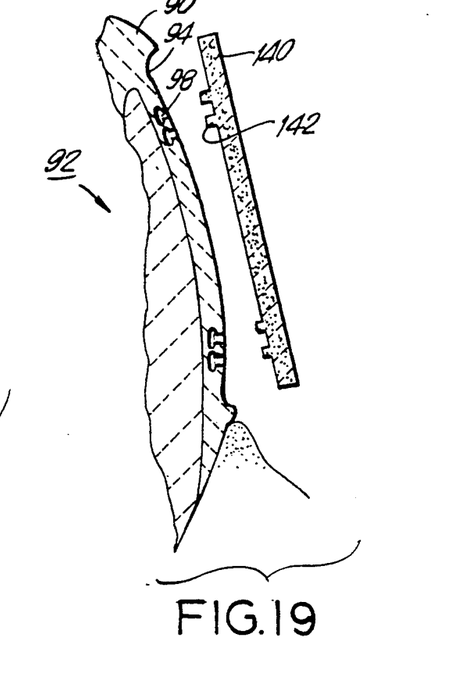
FIG. 19 shows an alternate arrangement where the adhesive film includes the projecting torroidal plugs.

As shown in FIG. 19, the single adhesive strip 140 already includes the torroidal adhesive plugs 142 projecting directly from one surface thereof. The adhesive strip 140 Would include the appropriate backing sheets and would then be positioned directly in place with the torroidal plugs already connected to the strip and secured within the torroidal indents.

Figures 20, 21:
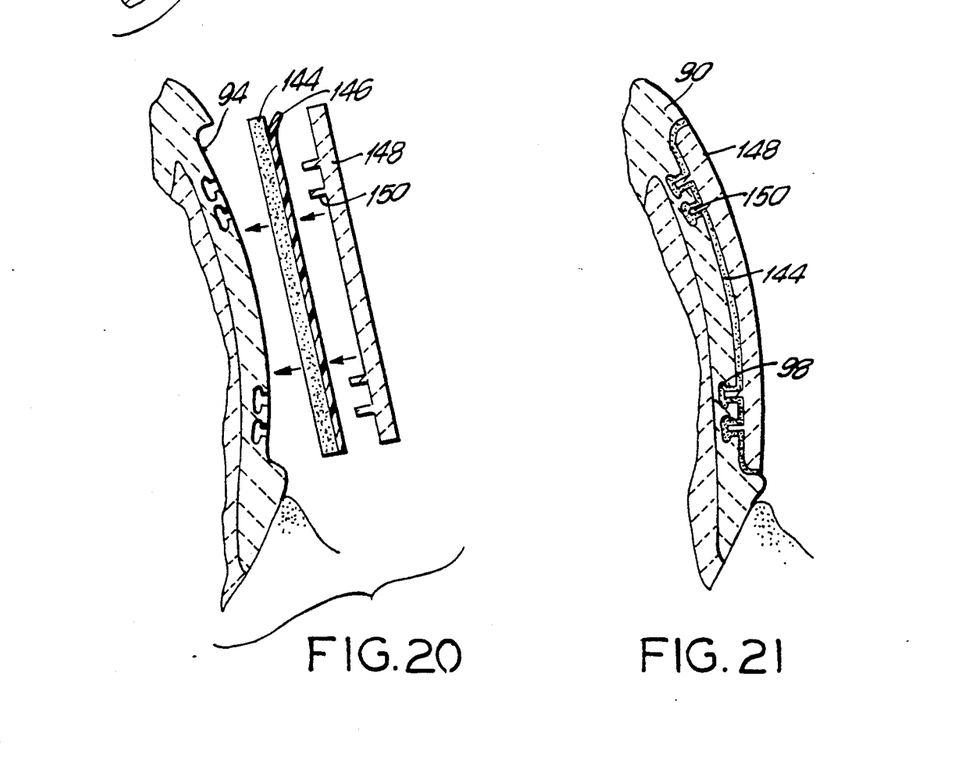
FIGS. 20 and 21 show the arrangement where the inlay includes projecting plugs and the adhesive material is squeeze into the torroidal indents in applying the inlay onto the dental surface.

As shown in FIG. 20, it is also possible to use just the standard thin strip adhesive material 144 which will be positioned within the recess 94. Even though the torroidal indents 98 are provided, initially the strip 144 would just be placed directly over the indents without entering into them. After positioning in place, the backing strip 146 would be removed. At this point, the inlay 148 would be applied. However, the inlay would be cast to include torroidal plugs 150. These would serve to push the adhesive material 144 into the indents 98 filling the indents and providing a greater retention, as shown in FIG. 21.

It should be appreciated, as shown in FIG. 21 that even though the torroidal indents 98 have the undercut portions at their lower edges, the torroidal plugs from the inlay need not include such protrusions to match the undercuts. The adhesive material will flow upon pressure into these undercuts and fill the undercuts.

Utilizing the torroidal indents, there is achieved an accurate positioning of the inlay onto the enamel surface. At the same time, it also provides for greater retention by not only utilizing a chemical retention through the bonding agent, but a physical retention through securement within the indents. It should also be appreciated, that because of the presence of the indents, there is greater surface area for adhesion of the bonding material onto dental surface.

The particular shape of the torroidal indent is such as to provide a center post with a surrounding torroidal groove. The use of the center post provides a centering arrangement which keeps the inlay concentric and prevents it from sliding over the surface of the dental enamel.

Figure 22:
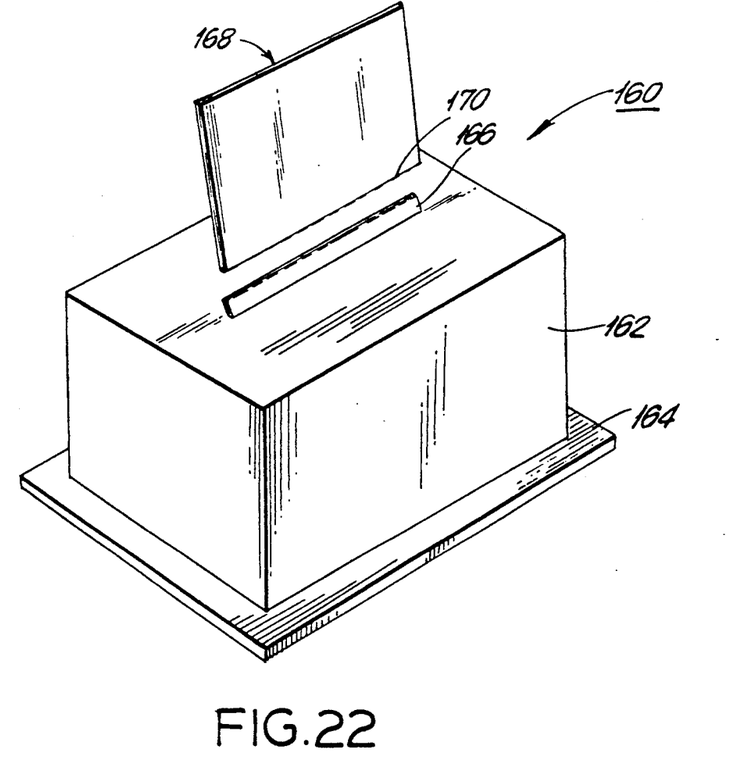
FIG. 22 shows a dispenser for dispensing the bonding arrangement of the present invention.

As shown in FIG. 22, the bonding arrangement heretofore provided can be dispensed through the use of a dispenser, typically shown at 160. The dispenser includes a housing 162 positioned on a base 164. An opening 166 is provided through which the bonding arrangement 168 projects. The bonding arrangement can be provided on a continuous strip with perforations 170 to permit ripping off one section from an adjacent section.

In the case of the bonding material being of a light cured type, the housing would be of a light impervious material to prevent light from entering into the housing while the bonding arrangement is stored within the housing to prevent curing of the adhesive material in the housing.

Figure 23:
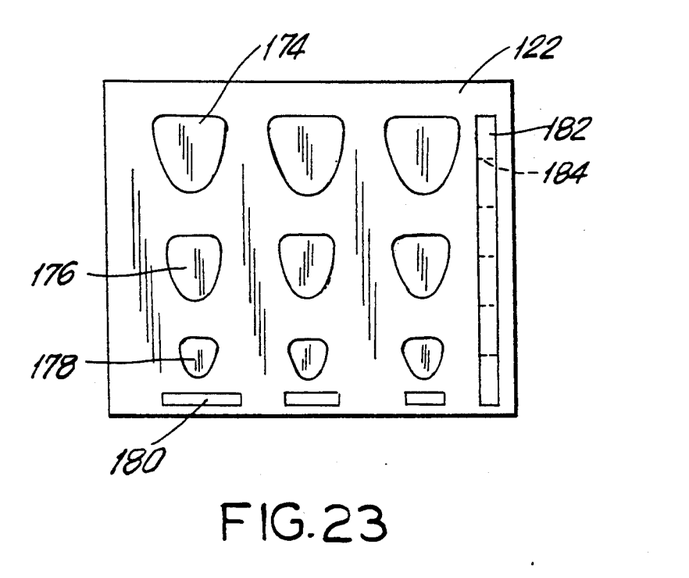
FIG. 23 shows a backing sheet having different sized adhesive films applied thereto and available for removal and utilization in the present invention.

As shown in FIG. 23, various shapes and types of the adhesive film can be provided. FIG. 23 shows a single backing sheet 172 on which there are individual strips of adhesive 174. The top backing sheet having been removed to expose the shape of the adhesive material. The adhesive can be formed in the shape of a tooth as shown at 174 with different sizes 176, 178 also provided. Individual elongated strips 180 can be provided, as can a single strip 182 with perforations 184 provided there along. The other backing sheet would be placed on top of it.

Figure 24:
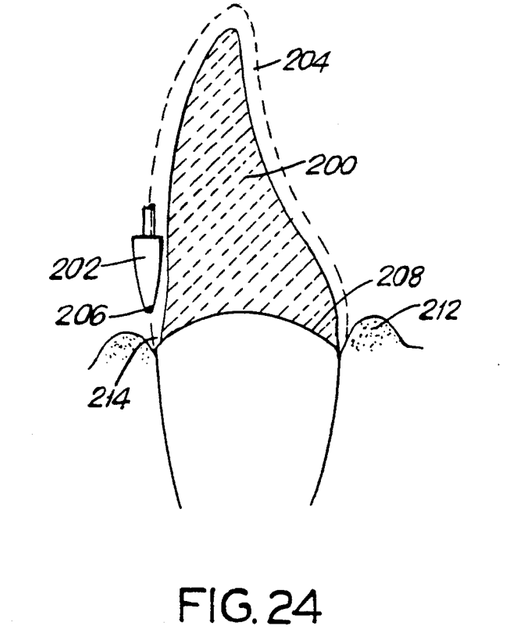
FIG. 24 shows the formation of a profile around the periphery of a tooth upon which a crown will be applied.

Refer now to FIG. 24, there is shown a tooth 200 whose profile has been cut down by means of a tool, schematically shown at 202 with the peripheral portion of the tooth 204 being removed in preparation of the placement of a crown. Such high speed tools are well-known and typically have a tapered forward end 206. As the forward end reaches the lower periphery 208 of the tooth near the gingiva 212, there is provided a tapered end portion 214 which comes to a rather sharp point at its lower marginal edge. Typically, a crown will then be formed to fit over the cut-down tooth. Because of the tapered marginal edge 214, the lower end of the crown portion will likewise have a very thin sharp edge to matingly fit onto this margin portion. The lower sharp edge of the crown, being very thin, may have a tendency to crack or split. Alternately, because of the sharp edge, as the crown is being seated, the edge may bite into the gingiva cutting it and causing damage to the gingival tissue. Occasionally, during continued use of the tooth with the crown on it, the crown may move slightly and again even during use, the crown on the tooth may cut down into the gingival area. This thin, sharp edge of the crown can be referred to as a feathering effect at the lower edge.

Figure 25:
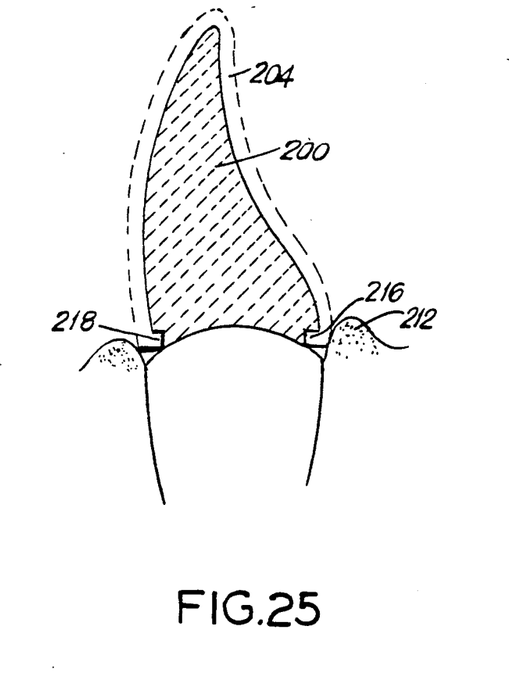
FIG. 25 shows the formation of lower ledges at the interface between the tooth and the gingiva with the inclusion of undercut shoulders adjacent the ledge.

Referring now to FIG. 25, the feathering effect of the thin lower edge of the crown can be eliminated by cutting a peripheral circumferential ledge 216 at the margin between the lower end of the tooth and the gingival interface. The margin can be formed through the use of a tool which cuts axially. At the same time, by forming a lateral forming cutting edge on the tool, a peripheral undercut shoulder 218 can be formed radially inwardly of the ledge.

Figure 26:
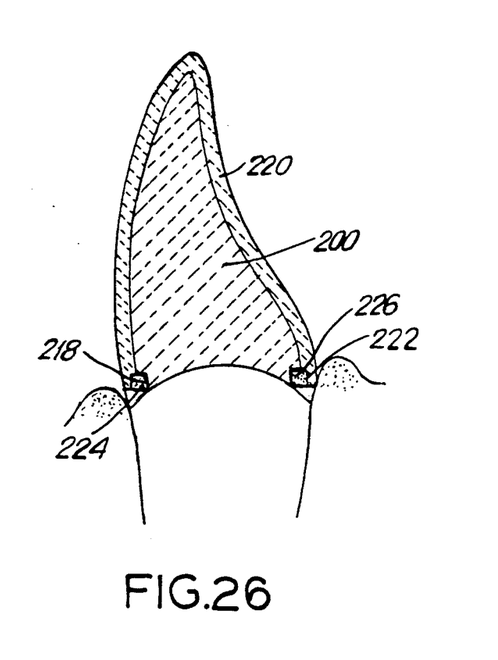
FIG. 26 is a view similar to that shown in FIG. 25 with the addition of a crown secured in place by the adhesive film serving as a gasket interface between the crown and the tooth.

As shown in FIG. 26, when the crown 220 is formed, a corresponding indented channel 222 can be formed to match the undercut shoulder portion 218 so as to define a peripheral passageway 224 about the lower marginal edge of the tooth 200. The adhesive film material previously described can be used as the bonding agent in this peripheral recess, as shown at 226.

In the formation of the crown, initially the lower ledge is cut at the marginal edge of the profile. The adhesive film material can then be placed within the undercut shoulder. The crown is then seated and the adhesive material will be extruded to fit within the recess defined between the undercut shoulder in the tooth and the peripheral channel in the crown.

The flat ledge at the marginal edge corresponds to the flat lower end of the crown so that the crown will appropriately seat onto the ledge. The ledge will form a stop-for-further seating of the crown thereby preventing the crown from biting into the gingiva. Even during continued use, it forms a lower stop limit for movement of the crown.

The presence of the adhesive material serves as a peripheral bonding ring for securing the crown onto the tooth. At the same time, because of the mating channels forming the recess, with the presence of the bonding agent hardening in place, the adhesive material also serves as a retaining ring while the channels and the bonding material form an interlock arrangement. As a result, the crown cannot be axially removed from the tooth surface.

Figure 27:
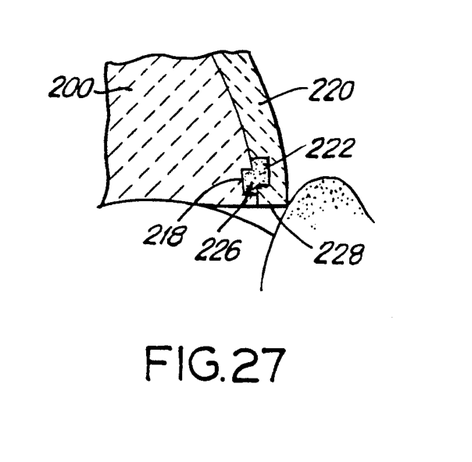
FIG. 27 is an enlarged view of the lower interface between the tooth, the gingiva, and the connected crown showing an offset arrangement of the panels to improve the interlock between the crown and the tooth.

As shown in FIG. 27, the undercut shoulder 218 can actually be slightly above the lower ledge 228. Likewise, the mating channel 222 can be offset from the undercut shoulder 218 in order to provide improved interlocking and prevent movement of the crown. The adhesive material 226 thereby forms both a bonding material, a gasket, as well as an interlocking retaining ring.

Figure 28:
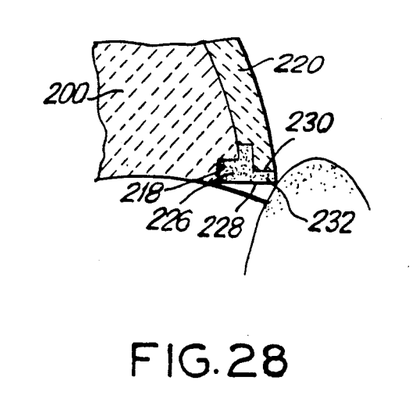
FIG. 28 is a view similar to that shown in FIG. 27 and further showing the extruded adhesive film beneath a shortened end of the crown to provide a circumferential seal.

As shown in FIG. 28, the lower end 230 of the crown 220 can be shortened from the bottom ledge 228. As a result, as the adhesive material 226 is put in place, and as the crown is seated, some of the adhesive material will extrude into the space above the ledge 228 and beneath the crown, as shown at 232 to provide a sealing ring about the periphery of the tooth. Such sealing ring would probably also be formed even without the shortened end of the crown. However, by shortening it we insure the adequacy of the sealing material.

Figure 29:
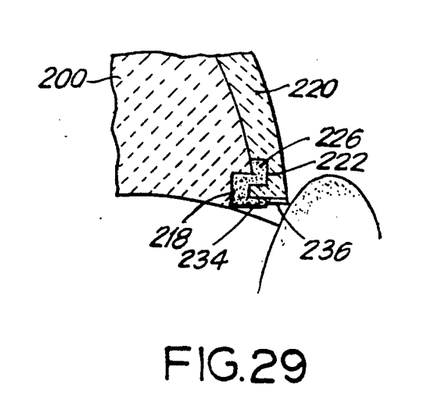
FIG. 29 is a view similar to that shown in FIG. 28 showing the formation of a peripheral trough along with the peripheral undercut shoulder for the retention of additional adhesive material in the formation of the gasket.

FIG. 29 shows the formation of a trough 234 along with the formation with the shoulder 218 as part of the undercut arrangement. This trough matches with the undercut 218 and the channel 222 to define a total recess in which the adhesive material 226 fills. Some of the adhesive material will likewise form a thin film layer 236 beneath the lower end of the crown 220.

The particular undercut shoulder can be approximately 1½ thousandths of an inch or 2 thousandths of an inch in depth, and about 5-8 thousandths of an inch in height. The lower end of the crown can be a few microns raised above the lower ledge or alternately, by cutting it shorter as much as 40 microns or even more, can be provided for adequate extrusion of the adhesive material. It should be appreciated, that these are only by way of examples and appropriate sizes would apply to the particular arrangement being used.

The presence of the gasket provides a ceiling for contamination, an interlock arrangement, additional retention, as well as bonding. The particular channel in the crown can be formed by having the dentist put a block around the periphery of the tooth when casting the crown. Alternately, a technician can utilize a tool which routes out the channel and the crown. Because of the presence of the adhesive layer, since this provides the retention it may not be necessary to use retention cement all along the surface area of the crown.

Figure 30:
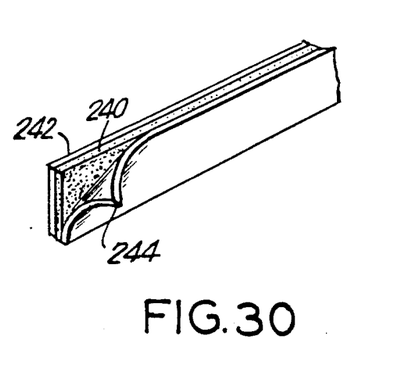
FIG. 30 is a perspective view of a strip of the adhesive film which can be wound around the periphery of the tooth to form the gasket shown in FIGS. 25-29.
Figure 31:
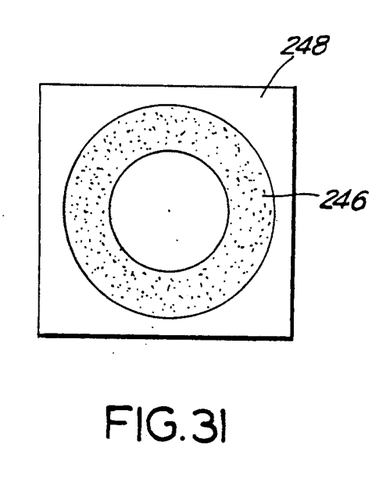
FIG. 31 shows a top view of a circular form of the adhesive film which can be utilized in a manner similar to that shown with the strip of FIG. 30

As shown in FIG. 30, the particular adhesive material for use in the embodiment shown in FIGS. 24-29 can be elongated strips 240 having a backing layer 242 on one side and a second backing layer 244 on the other side. Each of the backing layers would be removed to expose the elongated strips. The strips would then be wound about the periphery of the tooth and inserted in the undercut shoulder. Alternately, as shown in FIG. 31, the strips can be formed as a circular shape 246 mounted onto a backing surface 248. Another backing surface would be placed above the circular arrangement for removal prior to use. The circular arrangement can then be slipped about the undercut tooth and pressed into shape.

The backing sheets themselves can be transparent in order to view the size and shape of the adhesive material thereunder. Likewise, the adhesive material itself can be of a color different than the enamel in order to visually see the placement and the positioning.

There has been disclosed heretofore the best embodiment of the invention presently contemplated. However, it is to be understood that various changes and modifications may be made thereto without departing from the spirit of the invention.

I claim:

1. A dental bonding arrangement, comprising a film of viscous, self-supporting adhesive material, and a removable backing sheet on which the adhesive material is mounted, wherein said film is in the shape of a torroidal plug.

2. A dental bonding arrangement as in claim 1, and further comprising a second removable backing sheet on an opposite side of the adhesive material, wherein said film of adhesive material is sandwiched between said backing sheets.

3. A dental bonding arrangement as in claim 1, wherein said adhesive material is of the light curing type.

4. A dental bonding arrangement for attaching a dental inlay to a dental surface, comprising a semi-rigid layer of adhesive material of sufficient viscosity to permit contouring of the adhesive along the dental surface and of sufficient rigidity to maintain itself erect on the dental surface, and at least one backing sheet supporting the layer of adhesive material in a stored condition and from which the adhesive material can be peeled for use, wherein said adhesive material is in the configuration of a torroidal plug for insertion within a torroidal recess formed into the dental surface thereby improving the retention of the dental inlay.

5. A dental bonding arrangement for attaching a dental inlay to a dental surface formed within a recess, the arrangement comprising a semi-rigid layer of adhesive material of sufficient viscosity to permit contouring of the adhesive material along a surface of said recess and of sufficient rigidity to maintain itself erect on the surface of said recess to secure said inlay to said dental surface, and at least one backing sheet supporting the layer of adhesive material in a stored condition and from which the adhesive material can be peeled for use, wherein said adhesive material comprises a substantially planar layer, and at least one protruding torroidal plug projecting from said layer, the plug being capable of inserting within a corresponding torroidal recess formed into the dental surface to improve retention of the inlay.

6. A method of applying a dental inlay onto a dental surface, comprising the steps of
   a) preparing the tooth surface to accept the dental inlay by cutting a recess into a dental enamel for accommodating the inlay;
   b) applying a layer of adhesive material having a backing sheet thereon onto the prepared tooth surface;
   c) removing the backing sheet to expose the layer of adhesive material;
   d) applying the dental inlay onto the layer of adhesive material; and
   e) trimming the excess adhesive material beyond the edges of the dental inlay, as may be required.

7. A method as in claim 6, and wherein said step of preparing further includes cutting at least one torroidal indent into a bottom of the recess, and wherein the adhesive is of sufficient viscosity to fill the indents thereby improving the retention capabilities.

8. A method as in claim 7,, wherein the cutting of the indents includes forming undercuts at the bottom walls of the indents.

9. A method as in claim 7, and comprising the step of filling in the torroidal indent with a torroidal plug of adhesive material.

10. A method as in claim 9, wherein the torroidal plug of adhesive material has a backing sheet on at least one side thereof, and further comprising the step of peeling off the backing sheet after inserting the adhesive plug into the indent.

11. A method as in claim 9, wherein the torroidal plug is viscous enough to flow into undercuts formed at the bottom walls of the indent.

12. A method as in claim 7, wherein the sheet of adhesive comprises at least one adhesive plug protruding from a surface thereof for filling the torroidal indent.

13. A method as in claim 6, wherein the layer of adhesive material has a backing sheet on both sides thereof, one backing sheet being peeled off prior to use and the other backing sheet being peeled off after the adhesive is contacted to the dental surface and prior to application of the dental inlay.

14. A method as in claim 6, wherein the layer of adhesive material is of the light curing type, and further comprising the step of light curing the adhesive material to secure the dental inlay in place.

* * * * *